United States Patent
Abe et al.

(10) Patent No.: US 12,187,676 B2
(45) Date of Patent: Jan. 7, 2025

(54) METHOD FOR PRODUCING A CATALYST FOR UNSATURATED CARBOXYLIC ACID SYNTHESIS

(71) Applicant: Mitsubishi Chemical Corporation, Chiyoda-ku (JP)

(72) Inventors: Yoshimune Abe, Chiyoda-ku (JP); Nariyasu Kanuka, Chiyoda-ku (JP); Shigeki Okada, Chiyoda-ku (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 628 days.

(21) Appl. No.: 17/599,052

(22) PCT Filed: Mar. 27, 2020

(86) PCT No.: PCT/JP2020/014072
§ 371 (c)(1),
(2) Date: Sep. 28, 2021

(87) PCT Pub. No.: WO2020/203789
PCT Pub. Date: Oct. 8, 2020

(65) Prior Publication Data
US 2022/0177401 A1    Jun. 9, 2022

(30) Foreign Application Priority Data

Mar. 29, 2019  (JP) .................................. 2019-067228
Mar. 26, 2020  (JP) .................................. 2020-055290

(51) Int. Cl.
| | | |
|---|---|---|
| *C07C 51/25* | (2006.01) |
| *B01J 23/887* | (2006.01) |
| *B01J 37/00* | (2006.01) |
| *B01J 37/04* | (2006.01) |
| *B01J 37/08* | (2006.01) |

(52) U.S. Cl.
CPC ......... *C07C 51/252* (2013.01); *B01J 23/8877* (2013.01); *B01J 37/0036* (2013.01); *B01J 37/04* (2013.01); *B01J 37/082* (2013.01)

(58) Field of Classification Search
CPC ...... C07C 51/252; B01J 23/8877; B01J 37/04
See application file for complete search history.

(56) References Cited

U.S. PATENT DOCUMENTS

| | | | |
|---|---|---|---|
| 5,532,199 A | 7/1996 | Watanabe et al. | |
| 5,856,259 A | 1/1999 | Watanabe et al. | |
| 6,762,148 B2* | 7/2004 | Ohishi ................ | B01J 37/0215 502/305 |
| 2006/0063951 A1 | 3/2006 | Yunoki et al. | |
| 2016/0244393 A1* | 8/2016 | Kurakami ............ | B01J 23/8885 |
| 2019/0262806 A1* | 8/2019 | Tamura .................... | B01J 23/28 |

FOREIGN PATENT DOCUMENTS

| | | |
|---|---|---|
| EP | 3 056 482 A1 | 8/2016 |
| JP | 6-381 A | 1/1994 |
| JP | 8-238433 A | 9/1996 |
| JP | 2000-237592 A | 9/2000 |
| JP | 2001-96162 A | 4/2001 |
| JP | 2004-243213 A | 9/2004 |
| JP | 2011-152543 A | 8/2011 |
| JP | 2011-240219 A | 12/2011 |
| JP | 2012-20240 A | 2/2012 |
| JP | 2018-158287 A | 10/2018 |

OTHER PUBLICATIONS

Extended European Search Report issued Apr. 13, 2022 in European Patent Application No. 20783168.6, 7 pages.
International Search Report issued Jun. 9, 2020 in PCT/JP2020/014072 filed Mar. 27, 2020, 3 pages.
English translation of International Preliminary Report on Patentability and Written Opinion issued Sep. 28, 2021 in PCT/JP2020/014072, 10 pages.

* cited by examiner

Primary Examiner — Yate' K Cutliff
(74) Attorney, Agent, or Firm — Oblon, McClelland, Maier & Neustadt, L.L.P.

(57) ABSTRACT

A method for producing a catalyst for unsaturated carboxylic acid synthesis is proposed. The method includes: obtaining a dried product by drying and heat-treating a starting material mixed liquid in which supply source compounds of respective catalyst component elements are integrated; and forming a catalyst precursor by supporting powder to be supported on a carrier in the form of a particle aggregate. The powder to be supported is either the dried product or obtained from the dried product. The method further includes calcining the catalyst precursor to form the catalyst. The mass loss rate of the powder to be supported at 300° C. is less than 5 percent by mass, and the difference between the mass loss rate of the powder at 370° C. and the mass loss rate of the powder at 300° C. is not less than 1 percent by mass and not more than 6 percent by mass.

20 Claims, No Drawings

METHOD FOR PRODUCING A CATALYST FOR UNSATURATED CARBOXYLIC ACID SYNTHESIS

CROSS-REFERENCE TO RELATED APPLICATIONS

The present application is the national stage of international application PCT/JP2020/014072, filed on Mar. 27, 2020, and claims the benefit of the filing date of Japanese Appl. No. 2019-067228, filed on Mar. 29, 2019, and Japanese Appl. No. 2020-055290, filed on Mar. 26, 2020.

TECHNICAL FIELD

The present invention relates to a method for producing a catalyst for unsaturated carboxylic acid synthesis, more particularly a catalyst used to produce an unsaturated carboxylic acid by gas phase catalytic oxidation of an unsaturated aldehyde with oxygen-containing gas.

BACKGROUND ART

As catalysts used to produce unsaturated carboxylic acids by gas phase catalytic oxidation of an unsaturated aldehyde with oxygen-containing gas, catalysts containing molybdenum as an essential component are typically used. In particular, various trials are being vigorously made to improve catalysts used to produce acrylic acid, which is made from, e.g., acrolein, or methacrylic acid, which is made from, e.g., methacrolein, as well as to improve the methods for producing such catalysts.

The method for producing an unsaturated carboxylic acid comprises subjecting an olefine to gas phase catalytic oxidation with oxygen-containing gas in a fixed-bed reactor filled with a catalyst.

Examples of the catalyst filling the fixed-bed reactor include, for example, a catalyst obtained by forming powder of catalyst component elements into a predetermined shape, and a catalyst having catalyst component elements supported on an inert carrier having a predetermined shape.

The below-identified Patent Document 1 discloses using, as a catalyst used to produce an unsaturated carboxylic acid by subjecting an unsaturated aldehyde to gas phase catalytic oxidation, a catalyst obtained by supporting, on a carrier, powder obtained by mixing together, suspending, drying and pulverizing catalyst component elements including, as an essential element, molybdenum.

Patent Document 1 teaches that it is possible to improve the catalytic activity and the mechanical strength of the catalyst by using, for dried powder of the catalyst component elements, dried powder of which the mass loss rate in an air atmosphere of 300° C. is within a predetermined range.

PRIOR ART DOCUMENT

Patent Document

Patent Document 1: Japanese Unexamined Patent Publication 2004-243213A

However, the catalyst obtained in the above manner was not necessarily satisfactory in achieving the object of this publication, i.e., improving the raw material conversion rate and the selectivity of the end product.

An object of the present invention is therefore to provide a catalyst capable of further improving the raw material conversion rate and the end product selectivity.

Means for Achieving the Object

That is, the present invention provides the following:

[1] A method for producing a catalyst for unsaturated carboxylic acid synthesis, the method comprising:
(i) a drying step of obtaining a dried product by drying and heat-treating a starting material mixed liquid in which supply source compounds of respective catalyst component elements are integrated;
(ii) a forming step of forming a catalyst precursor by supporting powder to be supported on a carrier comprising a particle aggregate, the powder to be supported being either the dried product or obtained from the dried product; and
(iii) a calcining step of calcining the catalyst precursor to form the catalyst,
wherein a first mass loss rate of the powder to be supported at 300° C. is less than 5 percent by mass, and the difference between a second mass loss rate of the powder to be supported at 370° C. and the first mass loss rate of the powder to be supported at 300° C. is not less than 1 percent by mass and not more than 6 percent by mass, and
wherein the first and second mass loss rates of the powder to be supported are calculated from the following formula based on the masses of the powder to be supported before and after heating the powder to be supported to 300° C. and 370° C. in an air atmosphere until there is no change in mass:

mass loss rate (mass %)=[(mass of the powder to be supported before heating (g)−mass of the powder to be supported after heating (g))/mass of the powder to be supported before heating (g)]×100.

[2] A method for producing a catalyst for unsaturated carboxylic acid synthesis, the method comprising:
(i) a drying step of obtaining a dried product by drying and heat-treating a starting material mixed liquid in which supply source compounds of respective catalyst component elements are integrated;
(ii) a forming step of forming a catalyst precursor by supporting powder to be supported on a carrier comprising a particle aggregate, the powder to be supported being either the dried product or obtained from the dried product; and
(iii) a calcining step of calcining the catalyst precursor to form the catalyst,
wherein the heat-treating is carried out at a heat treatment temperature of not less than 270° C. and not more than 330° C. for not less than 30 minutes and not more than 3 hours.
[3] The method described in item [1] above, wherein the heat-treating is carried out at a heat treatment temperature of not less than 270° C. and not more than 330° C. for not less than 30 minutes and not more than 3 hours.
[4] The method described in any one of items [1] to [3] above, wherein the starting material mixed liquid contains sulfate.
[5] The method described in any one of items [1] to [4] above, further comprising the step of pulverizing the dried material.

[6] The method described in any one of items [1] to [5] above, wherein the catalyst is a catalyst represented by the following composition formula (1):

$$Mo_{12}V_aX_bCu_cY_dSb_eZ_fSi_gC_hO_i \quad (1)$$

(where X denotes Nb and/or W, Y denotes at least one element selected from the group consisting of Mg, Ca, Sr, Ba, and Zn, and Z denotes at least one element selected from the group consisting of Fe, Co, Ni, and Bi; and a to i denote atomic ratios of the respective elements, wherein a to h satisfy the relations: $0<a\leq 12$, $0\leq b\leq 12$, $0\leq c\leq 12$, $0\leq d\leq 8$, $0\leq e\leq 500$, $0\leq f\leq 500$, $0\leq g\leq 500$, and $0\leq h\leq 500$, and i is a value satisfying the oxidation state of the other elements).

[7] A method for producing acrylic acid by gas phase catalytic oxidation of acrolein with oxygen-containing gas using the catalyst produced by the method described in any one of items [1] to [6] above.

Advantages of the Invention

According to the present invention, due to the use of an unsaturated carboxylic acid synthesizing catalyst having a predetermined relationship between the mass loss rates at two predetermined temperatures, it is possible to increase the raw material conversion rate and the end product selectivity, thereby improving the yield.

Embodiment

Detailed description of an embodiment of the present invention is given below. It is to be understood that the present invention is not limited to what is described below, and can be modified in various ways and embodied, within the spirit of the invention.

<Catalyst>

A catalyst for synthesizing an unsaturated carboxylic acid according to the present invention (which is hereinafter sometimes simply referred to as the "catalyst") is used to produce an unsaturated carboxylic acid such as acrylic acid or methacrylic acid, by subjecting an unsaturated aldehyde such as acrolein or methacrolein as a raw material, to gas phase catalytic oxidation using an oxygen-containing gas.

The catalyst contains molybdenum (Mo) as an essential element, and preferably contains, as other catalyst component elements, vanadium (V) and copper (Cu). Further preferably, the catalyst contains one or a plurality of elements selected from antimony (Sb), silicon (Si), carbon (C), niobium (Nb), tungsten (W), magnesium (Mg), calcium (Ca), strontium (Sr), barium (Ba), zinc (Zn), iron (Fe), cobalt (Co), nickel (Ni), bismuth (Bi), etc.

One example of such a catalyst is expressed by the following composition formula (1).

$$Mo_{12}V_aX_bCu_cY_dSb_eZ_fSi_gC_hO_i \quad (1)$$

In formula (1): X denotes Nb and/or W; Y denotes at least one element selected from the group consisting of Mg, Ca, Sr, Ba and Zn; and Z denotes at least one element selected from the group consisting of Fe, Co, Ni and Bi. The letters "a" to "i" denote the atomic ratios of the respective elements; the letters "a" to "h" are within the ranges of: $0<a\leq 12$; $0\leq b\leq 12$; $0\leq c\leq 12$; $0\leq d\leq 8$; $0\leq e\leq 500$; $0\leq f\leq 500$; $0\leq g\leq 500$; and $0\leq h\leq 500$, respectively; and the letter "i" is a value that satisfies the oxidized states of the other elements.

<Method of Producing the Catalyst>

Now a method of producing the above-described catalyst is described.

The method of producing the catalyst comprises: (i) a liquid preparation step in which, using predetermined compounds having elements as the components of the catalyst (these elements are hereinafter referred to as the "catalyst component elements"), as compounds which constitute supply sources of the catalyst (such compounds are hereinafter referred to as the "supply source compounds"), the supply source compounds having the catalyst component elements are added into solvents or solutions for integration, to obtain a starting material mixed liquid; (ii) a drying step of subjecting the starting material mixed liquid to heat treatment to obtain a dried product; (iii) a forming step of supporting the dried product as powder to be supported, or supporting powder to be supported that is obtained from the dried product, on a carrier comprising a particle aggregate, thereby forming a catalyst precursor; and (iv) a calcining step of calcining the catalyst precursor to form the catalyst.

[Liquid Preparation Step]

Supply source compounds containing one or a plurality of the above-mentioned catalyst component elements to be used, such as molybdenum, are integrated to obtain the starting material mixed liquid. The starting material mixed liquid may be a solution or a suspension.

The term "integration" or "integrated" refers to mixing or maturing, all at once or in a stepwise manner, aqueous solutions or aqueous dispersions of the supply source compounds for the above catalyst component elements. Specifically, the integration of the supply source compounds of the above catalyst component elements may be realized by any one, or a combination, of the following methods:

(a) Mixing together the supply source compounds all at once;
(b) Mixing together and maturing the supply source compounds, all at once;
(c) Mixing the respective supply source compounds in a stepwise manner; and
(d) Mixing and maturing the respective supply source compounds in a stepwise manner.

"Maturing" refers to "an operation of processing industrial raw materials or half-finished products under specific conditions, such as for a predetermined time period or at a predetermined temperature, to obtain or increase necessary physical properties or chemical properties, or to advance a predetermined reaction" (Encyclopedic Dictionary of Chemistry; Kyoritsu Shuppan Co., Ltd.). In the present invention, the above-mentioned "predetermined time period" refers to a time period within the range of not less than 10 minutes and not more than 24 hours, and the above-mentioned "predetermined temperature" refers to a temperature within the range of room temperature to the boiling point of the aqueous solutions or aqueous dispersions.

[Heat Treatment]

The starting material mixed liquid obtained by the above integration is used as it is or by heating, as the starting material mixed liquid. The heat treatment is a process of forming metallic oxides or composite metallic oxides of the individual supply source compounds of the above-mentioned catalyst component elements; forming a metallic oxide or composite metallic oxide of a composite compound produced by the integration; or forming a final composite metallic oxide. The heating is not limited to once. That is, the heating may be carried out at any one or ones of the integration stages shown as (a) to (d) above. If necessary, the heating may also be additionally performed after the integration. The heating temperature is within the range of 200° C. to 600° C.

Further, if necessary, the above-described integration and heating may be performed, besides the above-described periods, before, after or during, e.g., the above-described drying step or a pulverizing step.

[Supply Source Compounds]

Examples of the above-described supply source compound for molybdenum (Mo) include, for example, ammonium paramolybdate, molybdenum trioxide, molybdates, ammonium phosphomolybdate, and phosphomolybdates.

Examples of the above-described supply source compound for vanadium (V) include, for example, ammonium paramolybdate, vanadium pentoxide, vanadium oxalate, and vanadium sulfate.

In the above composition formula (1), in which the content of molybdenum is 12, the addition amount a of vanadium is preferably more than 0 and not more than 12, more preferably not less than 0.1 and not more than 6, and further preferably not less than 1 and not more than 5. By limiting the amount a within these ranges, the catalyst is high in conversion rate, and capable of producing an unsaturated carboxylic acid with high selectivity.

Examples of the above-described supply source compound for niobium (Nb) include, for example, niobium hydroxide, and niobium pentoxide. Examples of the above-described supply source compound for tungsten (W) include, for example, tungstates and their salts.

In the above composition formula (1), in which the content of molybdenum is 12, the addition amount b of the at least one element X selected from niobium and tungsten is preferably 0 or more and not more than 12, more preferably not less than 0.1 and not more than 6, and further preferably not less than 0.5 and not more than 4. By limiting the amount b within these ranges, the catalyst is high in conversion rate, and capable of producing an unsaturated carboxylic acid with high selectivity.

Examples of the above-described supply source compound for copper (Cu) include, for example, copper sulfate, copper nitrate, and cuprous chloride.

In the above composition formula (1), in which the content of molybdenum is 12, the addition amount c of copper is preferably more than 0 and not more than 12, more preferably not less than 0.1 and not more than 6, and further preferably not less than 0.5 and not more than 4. By limiting the amount c within these ranges, the catalyst is high in conversion rate, and capable of producing an unsaturated carboxylic acid with high selectivity.

Examples of the above-described supply source compound for magnesium (Mg) include, for example, magnesium oxide, magnesium carbonate, and magnesium sulfate. Examples of the above-described supply source compound for calcium (Ca) include, for example, calcium oxide, calcium carbonate, and calcium hydroxide. Examples of the above-described supply source compound for strontium (Sr) include, for example, strontium oxide, strontium carbonate, strontium hydroxide, and strontium nitrate. Examples of the above-described supply source compound for barium (Ba) include, for example, barium oxide, barium carbonate, barium nitrate, barium acetate, and barium sulfate. Examples of the above-described supply source compound for zinc (Zn) include, for example, zinc oxide, zinc carbonate, zinc hydroxide, and zinc nitrate.

In the above composition formula (1), in which the content of molybdenum is 12, the addition amount d of the at least one element Y selected from magnesium, strontium, barium and zinc is preferably 0 or more and not more than 8, more preferably not less than 0.1 and not more than 6, and further preferably not less than 0.2 and not more than 4. By limiting the amount d within these ranges, the catalyst is high in conversion rate, and capable of producing an unsaturated carboxylic acid with high selectivity.

Examples of the above-described supply source compound for antimony (Sb) include, for example, antimony trioxide, and antimony pentoxide.

In the above composition formula (1), in which the content of molybdenum is 12, the addition amount e of antimony is preferably 0 or more and not more than 500, more preferably not less than 0.1 and not more than 100, and further preferably not less than 0.2 and not more than 50. By limiting the amount e within these ranges, the catalyst is high in conversion rate, and capable of producing an unsaturated carboxylic acid with high selectivity.

Examples of the above-described supply source compound for iron (Fe) include, for example, ferric nitrate, ferric sulfate, ferric chloride, and ferric acetate. Examples of the above-described supply source compound for cobalt (Co) include, for example, cobalt nitrate, cobalt sulfate, cobalt chloride, cobalt carbonate, and cobalt acetate.

Examples of the above-described supply source compound for nickel (Ni) include, for example, nickel nitrate, nickel sulfate, nickel chloride, nickel carbonate, and nickel acetate. Examples of the above-described supply source compound for bismuth (Bi) include, for example, bismuth chloride, bismuth nitrate, bismuth oxide, and bismuth subcarbonate.

In the above composition formula (1), in which the content of molybdenum is 12, the addition amount f of the at least one element Z selected from cobalt, nickel and bismuth is preferably 0 or more and not more than 500, more preferably not less than 0.1 and not more than 400, and further preferably not less than 1 and not more than 300. By limiting the amount f within these ranges, the catalyst is high in conversion rate, and capable of producing an unsaturated carboxylic acid with high selectivity.

Examples of the above-described supply source compound for silicon (Si) include, for example, silica, granular silica, colloidal silica, and fumed silica.

In the above composition formula (1), in which the content of molybdenum is 12, the addition amount g of silicon is preferably 0 or more and not more than 500, more preferably not less than 0.1 and not more than 400, and further preferably not less than 1 and not more than 300. By limiting the amount g within these ranges, the catalyst is high in conversion rate, and capable of producing an unsaturated carboxylic acid with high selectivity.

Examples of the above-described supply source compound for carbon (C) include, for example, green silicon carbide and black silicon carbide, in which carbon (C) and Si are integrated, and such silicon carbide is preferably in the form of fine powder.

In the above composition formula (1), in which the content of molybdenum is 12, the addition amount h of carbon is preferably 0 or more and not more than 500, more preferably not less than 0.1 and not more than 400, and further preferably not less than 1 and not more than 300. By limiting the amount f within these ranges, the catalyst is high in conversion rate, and capable of producing an unsaturated carboxylic acid with high selectivity.

Preferably, one of these supply source compounds is preferably sulfate. That is, the above-described starting material mixed liquid preferably contains sulfate. By using a supply source compound having sulfate, the below-described dried product contains sulfate, and the powder to be supported also contains sulfate. This sufficiently contributes to improvement in the material conversion rate of the catalyst obtained, and selectivity of the end product.

[Drying Step]

The above-described drying step is a step of obtaining a dried product by drying, and then heating, the starting material mixed liquid obtained during the above-described liquid preparation step.

The drying step is not limited, and may be typically drum drying or spray drying. For example, spray drying is a preferred method in the present invention because, with the spray drying, the dried product is obtained in a short period of time from the starting material mixed liquid, and the dried product obtained is powder particles close in shape to spheres, and thus has high flowability.

Though varies depending on the concentrations of the supply source compounds in the starting material mixed liquid, the feed rate, and other factors, the temperature of the spray drying is ordinarily not less than 90° C. and not more than 250° C., and preferably not less than 120° C. and not more than 200° C. If the temperature is outside these ranges, the dried product may contain an excessive amount of water, or the recovery rate of the dried product could decline.

The above-described heat treatment is a heating process conducted preferably in the atmosphere at a predetermined temperature for a predetermined period of time.

The temperature of the heat treatment needs to be not less than 270° C., and is preferably not less than 280° C. Also, this temperature needs to be not more than 330° C., and is preferably not more than 320° C. If the temperature is outside this temperature range, no sufficient improvement may be obtained in terms of the material conversion rate of the catalyst obtained or the selectivity of the end product, or formation may become difficult.

The duration of such heat treatment needs to be not less than 30 minutes, and is preferably not less than 45 minutes. Also, this duration needs to be not more than 3 hours, and preferably not more than 2 hours. If this duration is outside the above range, no sufficient improvement may be obtained in terms of the material conversion rate of the catalyst obtained or the selectivity of the end product, or formation may become difficult.

Devices usable for such heat treatment include, for example, a box-shaped furnace, tunnel-shaped furnace, a hot-air dryer, and a rotary kiln. Among them, a hot-air dryer or a rotary kiln provides uniform heating of the dried product, and is thus preferable.

[Pulverizing Step]

The dried product obtained in the above-described drying step may be sent to the next step as it is. However, because the dried product is supported on the carrier in the next forming step, if the dried product is large in particle size, the dried product may be pulverized in a pulverizing step into a pulverized powder product. The pulverization may be carried out using, e.g., a pulverizer with agitating blades, a ball mill, a jet mill, or a hammer mill. Commercially available pulverizing devices include "WONDER BLENDER (Model No. WB-1) and "WONDER CRUSHER/MILL" (Model No. D3V-10), imported and sold by Osaka Chemical Co., Ltd.

[Forming Step]

In the above-described forming step, a catalyst precursor is obtained by using, as powder to be supported, the dried product obtained in the above-described drying step, or the above-described pulverized product. If the dried product obtained in the drying step is in the form of powder of which the particle size is small enough such that the dried product can be supported by the carrier, the dried product is used as it is as the powder to be supported. If the particle size of the dried product is too large, the pulverized powder product obtained by pulverizing the dried product in the pulverizing step is used as the powder to be supported.

The powder to be supported possesses a catalytic activity as it is. However, because a catalyst is ordinarily placed in a fixed-bed reactor, and used for gas phase catalytic oxidation, if the powder is used as it is as a catalyst, this may result in deterioration in workability when placing and removing such powder into and from the reactor, or an increase in pressure loss during catalytic oxidation in a gas phase. Thus, a catalyst is used which is formed by supporting the powder on a carrier comprising a particle aggregate. The major axis diameter of the thus-formed catalyst is preferably not less than 2 mm and not more than 15 mm, more preferably not less than 3 mm and not more than 10 mm.

The forming step is carried out by supporting the obtained power to be supported, on a carrier comprising a particle aggregate. In order to easily support the powder to be supported on the carrier comprising a particle aggregate, and in order to improve the strength of the catalyst produced, additives such as, for example, a binder, a forming assistant, and a strength improver may be added. The carrier comprising a particle aggregate is preferably a carrier inactive to the reaction used as a catalyst. Examples of such carriers include silica, silicon carbide, alumina, alumina-silica, mullite and Alundum. Preferably, the carrier is, for example, a spherical carrier having normal axis diameters of preferably not less than 2.5 mm and not more than 10 mm, more preferably not less than 2.5 mm and not more than 6 mm. Further, in order for the carrier to be able to easily support the catalyst forming elements, the carrier has preferably a porosity of not less than 20% and not more than 60% and a water absorption rate of not less than 10% and not more than 60%.

The above-mentioned additives may be:
(1) added while being mixed beforehand in the powder to be supported;
(2) added when the powder to be supported is added into the fixed container;
(3) added after the powder to be supported is added; or
(4) added before the powder to be supported is added; or
(5) The powder to be supported and the additives are divided, and the divided portions are added separately.

Otherwise, the entire powder to be supported and additives may be added by combining some or all of (1) to (5) above. For (5) above, the powder to be supported and the additives are preferably added while adjusting the addition rate using, e.g., an Auto-Feeder such that a predetermined amount of the powder to be supported is supported on the carrier without adhering to the fixed container wall, and without aggregation of the powder particles to be supported.

The content ratio between the powder to be supported and the carrier is determined such that the amount of the powder to be supported relative to the total amount of the powder to be supported and the carrier is normally not less than 10 percent by mass or more and not more than 90 percent by mass, preferably not less than 20 percent by mass and not more than 70 percent by mass.

The catalyst precursor obtained by the above-described method preferably has a major axis diameter of not less than 3 mm and not more than 12 mm, more preferably not less than 3 mm and not more than 7 mm.

Examples of the above-mentioned binder include organic binders such as ethanol, glycerin and polyvinyl alcohol, and inorganic binders such as an aqueous solution of silica sol. Among them, an organic binder is preferable, and glycerin or polyvinyl alcohol is especially preferable. An organic binder may be used as it is, but for ease of handling, it is preferably used as an aqueous solution. The concentration of such an aqueous solution is preferably not less than 0.1 percent by mass. The amount of the binder used is, based on 100 parts by weight of the powder to be supported, normally not less than 0.1 parts by weight and not more than 50 parts by weight, preferably not less than 0.5 parts by weight and not more than 30 parts by weight.

Examples of the above-mentioned forming assistant include, for example silica gel, diatomaceous earth, and alumina powder. The amount of the forming assistant used is, based on 100 parts by weight of the powder to be supported, usually not less than 1 parts by weight and not more than 20 parts by weight. Also, using, where appropriate, a strength improver selected from, for example, scaly glass, ceramic fibers, whiskers or other inorganic substances would be beneficial in improving the mechanical strength of the catalyst. The amount of the strength improver used is, based on 100 parts by weight of the powder to be supported, usually not less than 0.5 parts by weight and not more than 20 parts by weight.

It is essential that the mass loss rate of the powder to be supported be within a predetermined range when subjected to heat treatment at a specific temperature right before being supported on the carrier comprising a particle aggregate. Specifically, the mass loss rate of the powder to be supported when subjected to heat treatment at 300° C. is less than 5 percent by mass, preferably less than 4 percent by mass. If the mass loss rate at 300° C. is larger than 5 percent by mass, it may become difficult to form the catalyst. Also, this may cause, during calcination, reduction of active catalytic components in the powder supported, which could in turn result in reduction in the catalytic activity, especially the raw material conversion rate.

In addition to the above requirement, it is essential that the difference between the mass loss rates when the powder to be supported is heat treated at 370° C. and at 300° C. be not less than 1 percent by mass and not more than 6 percent by mass, and preferably, this difference is not less than 2 percent by mass and 4 percent by mass. If the difference between the mass loss rates of the powder to be supported at 370° C. and 300° C. is greater than 6 percent by mass, the active catalytic components in the powder supported may decrease during calcination, resulting in a decrease in catalytic activity, especially in the raw material conversion rate. On the other hand, if the difference between the mass loss rates of the powder to be supported at 370° C. and 300° C. is less than 1 percent by mass, it may be difficult to create pores in the catalyst that are effective for the reaction, and the catalytic activity, especially the raw material conversion rate, may decrease.

The powder to be supported that satisfies these requirements can be obtained by appropriately adjusting the drying conditions during drying, the heating temperature, heating time, and other conditions during heat treatment, the conditions during the pulverizing step, and the environment (e.g., temperature) and the time until the obtained powder to be supported is supported on the carrier comprising a particle aggregate.

The mass loss rate of the above-described powder to be supported is calculated from the following formula based on the masses of the powder to be supported before and after heating the powder to be supported to 300° C. or 370° C. in an air atmosphere until there is no change in mass.

Mass loss rate (percent by mass)=[(mass of the powder to be supported before heating (g)−mass of the powder to be support after heating (g))/mass of the powder to be supported before heating (g)]×100

[Calcining Step].

The calcining step is a step in which the catalyst precursor obtained in the above-described forming step is calcined to form a catalyst.

That is, the catalyst precursor obtained in the forming step is then calcined to obtain the catalyst. The calcination temperature is usually between 250° C. and 800° C., preferably between 300° C. and 600° C., and the calcination time is not less than 1 hour and not more than 50 hours.

The catalyst produced by this method enables catalytic oxidation of unsaturated aldehydes such as acrolein and methacrolein with oxygen-containing gas in a gas phase to suitably produce unsaturated carboxylic acids such as acrylic acid and methacrylic acid at high conversion and high selectivity.

EXAMPLES

The present invention is described based on the following examples. The present invention is not limited in any way to these examples, and covers their modifications as long as they do not exceed the gist of the invention.

<Measurement of Mass Loss Rate>

1 g of the powder to be supported was, immediately before being supported on the carrier, weighed and placed in a crucible and held at a predetermined temperature in a muffle furnace for 1 hour in the presence of air. The mass loss rate at the predetermined temperature was calculated based on the masses of the powder before and after heating.

<Calculation of Conversion Rate, Selectivity, and Yield>

The acrolein conversion rate, acrylic acid selectivity, and acrylic acid yield were calculated from the following equations.

Acrolein conversion (mole %)=(number of moles of acrolein reacted/number of moles of acrolein supplied)×100

Acrylic acid selectivity (mole %)=(number of moles of acrylic acid produced/number of moles of acrolein converted)×100

Acrylic acid yield (mole %)=(number of moles of acrylic acid produced/number of moles of acrolein supplied)×100

Examples 1 to 3 and Comparative Examples 1 to 4

<Preparation of the Catalyst>

In each of Examples 1 to 3 and Comparative Examples 1 to 4, 2281 ml of warm water was placed in a vessel, and 76 g of ammonium metavanadate was added and dissolved. Then, 568 g of ammonium molybdate was added and dissolved to obtain a solution (hereinafter referred to as "Solution A").

Next, a solution of 80 g of copper sulfate dissolved in 115 ml of warm water was added to the solution A and mixed to obtain a uniformly mixed solution. Then, 52 g of niobium hydroxide and 16 g of antimony trioxide were added to the mixed solution, and the mixture was stirred to obtain the starting material mixed liquid.

This starting material mixed liquid was spray-dried at 150° C., and then heat-treated in the atmosphere using a hot-air dryer at the heat-treatment temperature listed in Table 1 for the holding time listed in Table 1 to obtain the dried product.

The dried product was pulverized to less than 200 μm using a pulverizer with agitating blades to obtain the pulverized product. This pulverized product was used as the powder to be supported. To this powder, 1.5% by weight of scaly glass was added, and they were uniformly mixed together. 100 g of spherical inert carrier of 4.9 mm in diameter, mainly composed of alumina-silica, was fed into a pan type granulator, and the mixture was added, alternately with 20% by weight aqueous solution of glycerin, such that the amount of the mixture supported was 40% by weight of the carrier. The catalyst precursor was thus obtained. The catalyst precursor was then calcined at 390° C. for 3 hours in an atmosphere of which air is diluted with nitrogen to 5% oxygen by volume. The composition ratio of the catalyst was as follows $Mo_{12}V_{2.4}Cu_{1.2}Nb_1Sb_{0.4}$ <Gas Phase Catalytic Oxidation of Acrolein>

A reaction tube with an inner diameter of 21 mm was filled with 33 ml of the above-described catalyst. Then, a raw material mixed gas obtained by adding oxygen and nitrogen to the gas obtained from the gas phase of propylene, and having the following composition, was introduced into the reaction tube through its inlet, and the reaction was evaluated at a space velocity of 1,550/hr. The heating medium temperature was 250° C. The results of the reaction evaluation are shown in Table 1.

The composition of the raw material mixed gas used is as follows:

acrolein: 6 volume %, steam: 22 volume %, oxygen: 8 volume %, (nitrogen-containing inert gas+other gases): 64 volume %.

wherein a difference between a second mass loss rate of the powder to be supported at 370° C. and the first mass loss rate is not less than 1 percent by mass and not more than 6 percent by mass, wherein the first mass loss rate and the second mass loss rate are calculated from formula (I) based on masses of the powder to be supported before and after heating the powder to be supported to 300° C. and 370° C., respectively, in an air atmosphere until there is no change in mass:

$$R_{ML}=(M_0-M_H)/M_0 \times 100 \tag{I}$$

wherein $R_{ML}$ is mass loss rate in percent by mass, $M_0$ is mass of the powder to be supported before heating in grams, and $M_H$ is mass of the powder to be supported after heating in grams, and wherein the catalyst comprises molybdenum as an essential component.

2. The method of claim 1, wherein the heat-treating in the obtaining (i) is carried out at a heat treatment temperature of not less than 270° C. and not more than 330° C. for not less than 30 minutes and not more than 3 hours.

3. The method of claim 1, wherein the starting material mixed liquid comprises sulfate.

4. The method of claim 1, further comprising:
pulverizing the dried material.

5. The method of claim 1, wherein the catalyst is of formula (1):

$$Mo_{12}V_aX_bCu_cY_dSb_eZ_fSi_gC_hO_i \tag{1}$$

wherein
X is Nb and/or W,

TABLE 1

|  |  | Example | | | Comparative Example | | | |
|---|---|---|---|---|---|---|---|---|
|  |  | 1 | 2 | 3 | 1 | 2 | 3 | 4 |
| Heat treatment temp. | (° C.) | 300 | 320 | 280 | 380 | Not heated | 340 | 260 |
| Duration | (Hr) | 1 | 1 | 1 | 1 | — | 1 | 1 |
| Mass loss rate A | (mass %) | 3.1 | 2.5 | 3.5 | 1.7 | 9.6 | 2.0 | 5.2 |
| Mass loss rate B | (mass %) | 6.3 | 4.6 | 7 | 1.9 | 13.7 | 2.8 | 8.6 |
| B − A | (mass %) | 3.2 | 2.1 | 3.5 | 0.2 | 4.1 | 0.8 | 3.4 |
| Acrolein conversion | (%) | 99.1 | 98.1 | 99.4 | 78.1 | Not formable | 85.7 | 87.0 |
| Acrylic acid selectivity | (%) | 95.4 | 95.2 | 94.6 | 96.5 |  | 96.5 | 96.7 |
| Acrylic acid yield | (%) | 94.5 | 93.4 | 94 | 75.4 |  | 82.7 | 84.1 |

In the table, "Mass loss rate A" represents the mass loss rate at 300° C., and "Mass loss rate B", at 370° C.

What is claimed is:

1. A method for producing a catalyst suitable for unsaturated carboxylic acid synthesis, the method comprising:
   (i) obtaining a dried product by drying and heat-treating a starting material mixed liquid in which supply source compounds of respective catalyst component elements are integrated;
   (ii) forming a catalyst precursor by supporting powder to be supported on a carrier comprising a particle aggregate, the powder to be supported being either the dried product or obtained from the dried product; and
   (iii) calcining the catalyst precursor to form the catalyst,
   wherein the heat-treating in the obtaining (i) is carried out at a heat treatment temperature of not less than 270° C. and not more than 330° C. for not less than 30 minutes and not more than 2 hours,
   wherein the powder to be supported, in the forming (ii), has a first mass loss rate, at 300° C., of less than 5 percent by mass, Y is Mg, Ca, Sr, Ba, and/or Zn,
Z is Fe, Co, Ni, and/or Bi,
a to i are atomic ratios satisfying relations:

$0 < a \leq 12$, $0 \leq b \leq 12$, $0 < c \leq 12$, $0 \leq d \leq 8$, $0 \leq e \leq 500$, $0 \leq f \leq 500$, $0 \leq g \leq 500$, and $0 \leq h \leq 500$, and i is a value satisfying the oxidation state of the other elements.

6. A method for producing acrylic acid, the method comprising:
catalytically oxidizing acrolein in gas phase with oxygen-containing gas, using the catalyst produced by the method of claim 1.

7. The method of claim 1, wherein the starting material mixed liquid comprises sulfate.

8. The method of claim 1, further comprising:
pulverizing the dried product from the obtaining (i).

9. The method of claim 2, further comprising:
pulverizing the dried product from the obtaining (i).

10. The method of claim 3, further comprising:
pulverizing the dried product from the obtaining (i).

11. The method of claim 7, wherein the catalyst is of formula (1):

$$Mo_{12}V_aX_bCu_cY_dSb_eZ_fSi_gC_hO_i \qquad (1),$$

wherein
X is Nb and/or W,
Y is Mg, Ca, Sr, Ba, and/or Zn, and
Z is Fe, Co, Ni, and/or Bi,
a to i are atomic ratios satisfying relations:

$0<a\leq12,$ $0\leq b\leq12,$ $0<c\leq12,$ $0\leq d\leq8,$ $0\leq e\leq500,$ $0\leq f\leq500,$ $0\leq g\leq500,$ $0\leq h\leq500,$ and i is a value satisfying the oxidation state of the other elements.

12. The method of claim 2, wherein the catalyst is of formula (1):

$$Mo_{12}V_aX_bCu_cY_dSb_eZ_fSi_gC_hO_i \qquad (1),$$

wherein
X is Nb and/or W,
Y is Mg, Ca, Sr, Ba, and/or Zn, and
Z is Fe, Co, Ni, and/or Bi,
a to i are atomic ratios satisfying relations:

$0<a\leq12,$ $0\leq b\leq12,$ $0<c\leq12,$ $0\leq d\leq8,$ $0\leq e\leq500,$ $0\leq f\leq500,$ $0\leq g\leq500,$ $0\leq h\leq500,$ and i is a value satisfying the oxidation state of the other elements.

13. The method of claim 3, wherein the catalyst is of formula (1):

$$Mo_{12}V_aX_bCu_cY_dSb_eZ_fSi_gC_hO_i \qquad (1),$$

wherein
X is Nb and/or W,
Y is Mg, Ca, Sr, Ba, and/or Zn, and
Z is Fe, Co, Ni, and/or Bi,
a to i are atomic ratios satisfying relations:

$0<a\leq12,$ $0\leq b\leq12,$ $0<c\leq12,$ $0\leq d\leq8,$ $0\leq e\leq500,$ $0\leq f\leq500,$ $0\leq g\leq500,$ $0\leq h\leq500,$ and i is a value satisfying the oxidation state of the other elements.

14. The method of claim 4, wherein the catalyst is of formula (1):

$$Mo_{12}V_aX_bCu_cY_dSb_eZ_fSi_gC_hO_i \qquad (1),$$

wherein
X is Nb and/or W,
Y is Mg, Ca, Sr, Ba, and/or Zn, and
Z is Fe, Co, Ni, and/or Bi,
a to i are atomic ratios satisfying relations:

$0<a\leq12,$ $0\leq b\leq12,$ $0<c\leq12,$ $0\leq d\leq8,$ $0\leq e\leq500,$ $0\leq f\leq500,$ $0\leq g\leq500,$ $0\leq h\leq500,$ and i is a value satisfying the oxidation state of the other elements.

15. A method for producing acrylic acid, the method comprising:
catalytically oxidizing acrolein in gas phase with oxygen-containing gas, using the catalyst produced by the method of claim 7.

16. A method for producing acrylic acid, the method comprising:
catalytically oxidizing acrolein in gas phase with oxygen-containing gas, using the catalyst produced by the method of claim 2.

17. A method for producing acrylic acid, the method comprising:
catalytically oxidizing acrolein in gas phase with oxygen-containing gas, using the catalyst produced by the method of claim 3.

18. A method for producing acrylic acid, the method comprising:
   catalytically oxidizing acrolein in gas phase with oxygen-containing gas, using the catalyst produced by the method of claim 4.

19. A method for producing acrylic acid, the method comprising:
   catalytically oxidizing acrolein in gas phase with oxygen-containing gas, using the catalyst produced by the method of claim 5.

20. The method of claim 1, wherein the heat-treating in the obtaining (i) is carried out at a heat treatment temperature of not less than 270° C. and not more than 330° C. for not less than 30 minutes and less than 1 hour.

* * * * *